(12) United States Patent
Huang

(10) Patent No.: US 12,285,510 B2
(45) Date of Patent: Apr. 29, 2025

(54) MILD CLEANSING COMPOSITION CONTAINING NEARLY SATURATED, SATURATED OR SUPERSATURATED ACTIVE INGREDIENTS AND PREPARATION METHOD THEREFOR

(71) Applicant: Yao-Kun Huang, Taoyuan (TW)

(72) Inventor: Yao-Kun Huang, Taoyuan (TW)

( * ) Notice: Subject to any disclaimer, the term of this patent is extended or adjusted under 35 U.S.C. 154(b) by 477 days.

(21) Appl. No.: 17/799,784

(22) PCT Filed: Feb. 19, 2020

(86) PCT No.: PCT/CN2020/075824
§ 371 (c)(1),
(2) Date: Aug. 15, 2022

(87) PCT Pub. No.: WO2021/163915
PCT Pub. Date: Aug. 26, 2021

(65) Prior Publication Data
US 2023/0091703 A1    Mar. 23, 2023

(51) Int. Cl.
| | |
|---|---|
| *A61K 8/44* | (2006.01) |
| *A61K 8/34* | (2006.01) |
| *A61K 8/86* | (2006.01) |
| *A61K 8/9728* | (2017.01) |
| *A61K 8/9789* | (2017.01) |
| *A61Q 19/00* | (2006.01) |
| *A61Q 19/10* | (2006.01) |

(52) U.S. Cl.
CPC ............... *A61K 8/44* (2013.01); *A61K 8/345* (2013.01); *A61K 8/442* (2013.01); *A61K 8/86* (2013.01); *A61K 8/9728* (2017.08); *A61K 8/9789* (2017.08); *A61Q 19/007* (2013.01); *A61Q 19/10* (2013.01)

(58) Field of Classification Search
None
See application file for complete search history.

(56) References Cited

FOREIGN PATENT DOCUMENTS

| | | |
|---|---|---|
| CN | 102198067 A | 9/2011 |
| CN | 102198078 A | 9/2011 |
| CN | 102488647 A | 6/2012 |
| CN | 102895316 A | 1/2013 |
| CN | 103040686 A | 4/2013 |
| CN | 103655448 A | 3/2014 |
| CN | 104523541 A | 4/2015 |
| CN | 104546607 A | 4/2015 |
| CN | 104800145 A | 7/2015 |
| CN | 105232437 A | 1/2016 |
| CN | 105326705 A | 2/2016 |
| CN | 105534809 A | 5/2016 |
| CN | 105560146 A | 5/2016 |
| CN | 108186440 A | 6/2018 |
| CN | 109528566 A | 3/2019 |

OTHER PUBLICATIONS

Ultimate Rehvdratina Facial Cleanser Record ID: 5546671 Company: Jahwa (Jiahua) Herborist Aqua Beauty Skincare Date Published: Apr. 2018.
Pore Deep Clearing Foam Record ID: 4739731 Company: Lan Cui Trading Manufacturer: Guangzhou Dong Fang Bio-Tech Date Published: Apr. 2017.
Clean It True Regulating Cleansing Gel Record ID: 2260560 Company: Parfums Givenchy Manufacturer: Parfums Givenchy Date Published: Dec. 2013.

*Primary Examiner* — Russell G Fiebig
(74) *Attorney, Agent, or Firm* — Troutman Pepper Locke LLP; Tim Tingkang Xia, Esq.

(57) ABSTRACT

A mild cleansing composition nearly saturated, saturated, or supersaturated with at least one active ingredient includes one or more surfactants and one or more active ingredients. The mild cleansing composition can be used to clean the skin and improve skin texture (e.g., the degree of radiance and wrinkles) at the same time.

16 Claims, 9 Drawing Sheets

MILD CLEANSING COMPOSITION CONTAINING NEARLY SATURATED, SATURATED OR SUPERSATURATED ACTIVE INGREDIENTS AND PREPARATION METHOD THEREFOR

BACKGROUND OF THE INVENTION

1. Technical Field

The present invention relates to a mild cleansing composition that is nearly saturated, saturated, or supersaturated with an active ingredient and to a method for preparing the same. More particularly, the invention relates to a cleaning and skin care composition that includes at least one surfactant and is nearly saturated, saturated, or supersaturated with at least one active ingredient for improving skin texture, and to a method for preparing the same.

2. Description of Related Art

Skin is the largest-area natural barrier of the human body against the external environment. To keep the skin in good hygienic conditions (i.e., in a clean and healthy state), a person should wash their skin in order to rid the skin of foreign matter coming from the environment where the person is or has been and the sebum and sweat secreted by the person's body. Skin cleaning, therefore, is the first and most important step of maintaining the health of skin. Take the cleaning of the face for example. A common cleaning product may be unable to clean the face thoroughly or may clean the face excessively such that either skin pores are clogged or the natural barrier of the skin is damaged (Indian J Dermatol. 2011 January-February; 56(1): 2-6). The temperature of the water used to wash the face, the duration of face washing, the choice of the cleaning product, and the cleaning method have their respective effects on the cleaning result and the maintenance of skin functions. It remains an issue to be addressed by researchers in the related fields to find a way to achieve thorough cleaning, maintain normal skin functions, and even enhance the skin esthetically at the same time.

The cleaning principles of cleaning preparations can be generally divided into dissolution and emulsification of dirt (Physicochemical and Engineering Aspects, 74, 169-215 (1993)). A cleaning preparation that removes dirt by dissolution inevitably cleans the skin surface to an excessive degree, resulting in damage of the skin barrier and roughness and dryness of the cleaned skin (Clinics in Dermatology, Volume 14, Issue 1, January-February 1996, Pages 29-33), or even over-secretion of sebum on the contrary. As to a cleaning preparation that removes dirt by emulsification, it is likely that the emulsifier does not remove the dirt completely, leaving a small amount of tiny emulsified particles that cannot be washed away but accumulate on the skin surface, in the pores, and in the sweat glands, causing a feel of uncleanliness, pore clogging, and the formation of acne.

The timing and method of applying a skin care product after skin cleaning can also be a challenge to the general public in their daily lives. While the timing of application of skin care products differs from one person to another, all such products can be analyzed in the following two aspects. First, the composition of a skin care product essentially includes water, oil, an emulsifier, a stabilizer, and various bases or even solvents. The emulsifier and the stabilizer are required because the two major ingredients that constitute most of the composition are an oil phase and a water phase, which are incompatible with each other. If an active ingredient is to be added into the composition, there are often challenges associated with physical and chemical stability, and the active ingredient is typically of such a low percentage that esthetic or clinical improvement of the skin is hard to achieve. Second, an important factor that influences, or limits, the absorption of a skin care preparation for external use is the barrier formed by the stratum corneum. The transdermal delivery system (TDDS) for a drug or cosmetic product generally has the following two paths: 1. penetrating the stratum corneum directly or through the lipid bilayers in the gaps between keratinocytes (this being the major path through the skin); and 2. passing through such skin appendages as hair follicles, sebaceous glands, or sweat glands (which appendages make up only 0.1% to 1.0% of the skin such that only an extremely small amount of active ingredient can be absorbed through this path). The major unsolved problems associated with the first absorption path are the acid mantle of the skin (Current Pharmaceutical Design, 2015, Vol. 21, No. 00) and the stratum corneum, which hinders absorption. Both the acid mantle and the stratum corneum are key barriers that block absorption of the active ingredients of drugs and cosmetic products, i.e., main factors that make it difficult for the users of skin care products to obtain the expected skin care effects.

BRIEF SUMMARY OF THE INVENTION

In view of the drawbacks of the existing cleaning and skin care techniques, the present invention aims to solve such prior art problems as difficulty in cleaning the skin with a mild composition and the difficulty in providing proper care for the skin, the objective being to provide a mild cleansing composition that can clean the skin, prevent excessive cleaning, and provide preliminary skin care at the same time in order to enhance skin functions. The invention provides a composition that is nearly saturated, saturated, or supersaturated with an active ingredient, that includes a mild surfactant, that is made by a simple manufacturing process, and that can clean the skin, prevent excessive cleaning, and provide skin care at the same time, wherein the active ingredient includes an extract of one or more selected from the group consisting of *Angelica dahurica*, *Ampelopsis japonica*, *Atractylodes macrocephala*, *Bletilla striata*, *Wolfiporia extensa*, *Aconitum carmichaelii*, and *Lithospermum erythrorhizon*, and wherein the surfactant includes one or more selected from the group consisting of a long-chain betaine, sodium lauroyl sarcosinate, sodium lauroyl methyl isethionate, and potassium cocoyl glycinate. The active-ingredient-containing mild cleansing composition of the invention can be used on any skin portion of the human body to clean the skin directly and provide skin care at the same time. The composition may produce one or a combination of the following effects on the skin: beautification by whitening, promoting the synthesis of collagen, reducing inflammation, preventing the skin from cracking due to dryness, relieving itchiness, preventing allergic reactions, preventing the appearance of aging, inhibiting oxidation, immunoregulation, and preventing fibrosis.

In the mild cleansing composition nearly saturated, saturated, or supersaturated with an active ingredient according to the present invention, the maximum concentration of each possible active ingredient, i.e., each distinctive or representative ingredient (or more particularly each fat-soluble and highly physiologically active ingredient) in an aqueous solution of the composition is as follows: *Angelica dahurica*≤0.01%, *Ampelopsis japonica*≤0.003%, *Atractylodes*

*macrocephala*≤0.004%, *Bletilla striata*≤0.006%, *Wolfiporia extensa*≤0.05%, *Aconitum carmichaelii*≤0.0002%, and *Lithospermum erythrorhizon*≤0.01%, meaning the maximum total concentration of all the aforesaid active ingredients is not higher than about 0.1%.

In the mild cleansing composition nearly saturated, saturated, or supersaturated with an active ingredient according to the present invention, the active ingredient may be prepared, or extracted, by one or a combination of a common high-temperature aqueous-solution-based extraction method, an organic-solvent-based extraction method, an ultrasonic extraction method, and a supercritical-fluid-based extraction method.

In the mild cleansing composition nearly saturated, saturated, or supersaturated with an active ingredient according to the present invention, the active ingredient may, according to the cosmetics laws and regulations of the U.S. Food and Drug Administration, satisfy the definitions of both cosmetics and drugs. In other words, based on its predetermined purpose of use as well as the disclosure of scientific journals, the composition of the invention may include any ingredient that can affect any function of a human or other animals. The composition of the invention, therefore, can be used to clean the human body, for cosmetic purposes, and so on.

In the mild cleansing composition nearly saturated, saturated, or supersaturated with an active ingredient according to the present invention, the active ingredient is preferably a substance intended to be rubbed, poured, sprayed, or sprinkled onto, introduced into, or applied by a wiping action to the human body in order to clean, beautify, increase the skin firmness of, or change the appearance of, the human body.

In the mild cleansing composition nearly saturated, saturated, or supersaturated with an active ingredient according to the present invention, the term "active ingredient" preferably refers to an ingredient that can produce one or a combination of the following effects on the skin: beautification by whitening, promoting the synthesis of collagen, reducing inflammation, preventing the skin from cracking due to dryness, relieving itchiness, preventing allergic reactions, preventing the appearance of aging, inhibiting oxidation, immunoregulation, and preventing fibrosis.

The mild cleansing composition nearly saturated, saturated, or supersaturated with an active ingredient according to the present invention may be in the dosage form of an oil-in-water (O/W) microemulsion (American Journal of Pharmtech Research, 2012), an emulsion, or a micelle solution (Cancers, July 2018), depending on the formula of the composition.

Pharmacologically, it is often required to maximize an active ingredient by way of dosage form design, in particular by using a liquid dosage form for a fat-soluble and highly physiologically active ingredient. For example, in order for the active ingredient (e.g., paclitaxel or docetaxel) of a taxol-containing drug to reach a therapeutically effective amount while the total administered volume of the drug is minimized, the dosage form of the drug is typically so designed that the concentration of the active ingredient is brought as close to the limit of the solubility of the active ingredient as possible. However, the drug being nearly saturated, saturated, or supersaturated with the active ingredient will disadvantageously make the active ingredient prone to precipitation when the drug is mixed with water. The present invention turns this disadvantage of near-saturation, saturation, or supersaturation with an active ingredient into the advantage of a cleaning preparation for external use such that, instead of being dissolved and washed away, the active ingredient of the cleaning preparation will be precipitated, and can be absorbed by the user's skin, after the preparation is mixed with water. In addition, with the cleaning preparation hydrating the user's skin, the absorption and effect of the active ingredient will be enhanced.

Indeed, the absorption of the active ingredient of the cleaning preparation can be enhanced by the cleaning preparation washing away the dirt on the skin and the acid mantle Penetration through the stratum corneum, however, requires a properly designed cosmeceutical delivery system in order to overcome the barrier against penetration through the gaps between, or directly through, keratinocytes (Skin Pharmacol Physiol 2006: 19: 106-21). The present invention uses a combination of mild surfactants that clean the skin and cause hydration of the stratum corneum by the emulsification method such that the hydrated stratum corneum has not only increased penetrability, but also increased capacitance. The invention takes advantage of this hydration phenomenon, whose occurrence helps enhance adsorption of the active ingredient and penetration of the active ingredient through the stratum corneum (The Journal of Investigative Dermatology, Vol. 101, No. 3, September 1993). In addition, as the concentration of the active ingredient reaches near-saturation, saturation, or supersaturation (Pharmaceutical Research, July 2001, Volume 18, Issue 7, pp 1006-1011), the active ingredient will easily precipitate, attach to the user's skin, and be absorbed by the skin due to a difference in concentration, thereby providing skin care as well as protection for the skin. This novel design principle also eliminates the possibility of the skin being excessively cleaned.

Researches and scientific literature have shown that long-chain betaines (Handbook for Cleaning/Decontamination of Surfaces), sodium lauroyl sarcosinate (Cosmetic Ingredient Review, September 2016), sodium lauroyl methyl isethionate (Cosmetic Ingredient Review, September 2013), and potassium cocoyl glycinate (Cosmetic Ingredient Review, September 2013) are mild and low-irritation surfactants as far as the skin and the eyes are concerned. The mild cleansing composition nearly saturated, saturated, or supersaturated with an active ingredient according to the present invention uses a combination of gently cleansing surfactants to clean the skin gently and dissolve the active ingredient to a concentration near saturation, of saturation, or of supersaturation so as to provide skin cleaning and skin care simultaneously.

To achieve the objective of cleaning the skin, preventing excessive cleaning, and providing skin care at the same time, the present invention provides a mild cleansing composition nearly saturated, saturated, or supersaturated with an active ingredient and a method for preparing the same. The cleansing composition includes at least one surfactant and at least one active ingredient that is present at a concentration near saturation, of saturation, or of supersaturation and that can improve the texture of skin. The at least one surfactant is one or an arbitrary combination of a long-chain betaine, sodium lauroyl sarcosinate, sodium lauroyl methyl isethionate, and potassium cocoyl glycinate, and makes up 5.00 wt % to 70.00 wt % of the composition of the invention. The at least one active ingredient is an extract of one or an arbitrary combination of *Angelica dahurica, Ampelopsis japonica, Atractylodes macrocephala, Bletilla striata, Wolfiporia extensa, Aconitum carmichaelii*, and *Lithospermum erythrorhizon*, and makes up 0.1 wt % to 10.00 wt % of the composition of the invention. The composition of the invention may further include an appropriate amount of water that makes up 15.00 wt % to 85.00 wt % of the composition of the invention. The composition of the invention may further include an appropriate amount of cosmetic excipient such as a thinner, a thickening agent, a stabilizer, a fragrance, a preservative, or a cosurfactant, with the excipient making up 0 wt % to 15.00 wt % of the composition of the invention.

Preferably, the at least one surfactant in the composition of the present invention includes a long-chain betaine, sodium lauroyl sarcosinate, sodium lauroyl methyl isethionate, and potassium cocoyl glycinate, which make up 0 wt % to 25.00 wt %, 0 wt % to 20.00 wt %, 0 wt % to 25.00 wt %, and 0 wt % to 20.00 wt % of the composition of the invention respectively, but whose total percentage by weight must not be zero.

More preferably, the at least one surfactant in the composition of the present invention is one or an arbitrary combination of a long-chain betaine, sodium lauroyl sarcosinate, sodium lauroyl methyl isethionate, and potassium cocoyl glycinate, and makes up 10.00 wt % to 65.00 wt % of the composition of the invention.

Even more preferably, the at least one surfactant in the composition of the present invention is one or an arbitrary combination of a long-chain betaine, sodium lauroyl sarcosinate, sodium lauroyl methyl isethionate, and potassium cocoyl glycinate, and makes up 20.00 wt % to 60.00 wt % of the composition of the invention.

Preferably, the at least one active ingredient of the composition of the present invention includes *Angelica dahurica, Ampelopsis japonica, Atractylodes macrocephala, Bletilla striata, Wolfiporia extensa, Aconitum carmichaelii,* and *Lithospermum erythrorhizon*, which make up 0 wt % to 8.00 wt %, 0 wt % to 8.00 wt %, 0 wt % to 8.00 wt %, 0 wt % to 4.00 wt %, 0 wt % to 4.00 wt %, 0 wt % to 4.00 wt %, and 0 wt % to 4.00 wt % of the composition of the invention respectively, but whose total percentage by weight must not be zero.

Preferably, the at least one active ingredient of the composition of the present invention is one or an arbitrary combination of *Angelica dahurica, Ampelopsis japonica, Atractylodes macrocephala, Bletilla striata, Wolfiporia extensa, Aconitum carmichaelii,* and *Lithospermum erythrorhizon*, and makes up 0.10 wt % to 8.00 wt % of the composition of the invention.

More preferably, the at least one active ingredient of the composition of the present invention is one or an arbitrary combination of *Angelica dahurica, Ampelopsis japonica, Atractylodes macrocephala, Bletilla striata, Wolfiporia extensa, Aconitum carmichaelii,* and *Lithospermum erythrorhizon*, and makes up 0.20 wt % to 6.00 wt % of the composition of the invention.

Even more preferably, the at least one active ingredient of the composition of the present invention is one or an arbitrary combination of *Angelica dahurica, Ampelopsis japonica, Atractylodes macrocephala, Bletilla striata, Wolfiporia extensa, Aconitum carmichaelii,* and *Lithospermum erythrorhizon*, and makes up 0.40 wt % to 4.00 wt % of the composition of the invention.

Preferably, the composition of the present invention further includes an appropriate amount of water that makes up 20.00 wt % to 80.00 wt % of the composition of the invention. The water more preferably makes up 25.00 wt % to 75.00 wt % of the composition of the invention, and even more preferably makes up 30.00 wt % to 70.00 wt % of the composition of the invention.

Preferably, the composition of the present invention further includes an appropriate amount of cosmetic excipient, and the excipient may be a thinner, a thickening agent, a stabilizer, a fragrance, a preservative, or a cosurfactant. The excipient, if included, may make up 0.50 wt % to 10.00 wt % of the composition of the invention, preferably 1.00 wt % to 8.00 wt % of the composition of the invention, more preferably 2.00 wt % to 6.00 wt % of the composition of the invention, and even more preferably 4.00 wt % to 6.00 wt % of the composition of the invention.

As stated above, the present invention provides a mild cleansing composition that is nearly saturated, saturated, or supersaturated with an active ingredient, and the composition includes at least one surfactant and at least one active ingredient that is present at a concentration near saturation, of saturation, or of supersaturation and is capable of improving skin texture. The mild cleansing composition is prepared by a method that includes the steps of: (i) adding the at least one active ingredient and an appropriate amount of water into a mixing container; (ii) adding the at least one surfactant into the mixing container in step (i), mixing the contents of the mixing container thoroughly, and if necessary, heating the contents until any undissolved portion of the contents is dissolved and thoroughly mixed; and (iii) if necessary, adding an appropriate excipient such as a thinner, thickening agent, stabilizer, fragrance, or preservative, continuing mixing until the contents of the mixing container are thoroughly mixed, and allowing the contents to cool down to room temperature.

Preferably, the mild cleansing composition nearly saturated, saturated, or supersaturated with an active ingredient according to the present invention and the method for preparing the same are such that the at least one active ingredient is prepared, or extracted, by one or an arbitrary combination of a common high-temperature aqueous-solution-based extraction method, an organic-solvent-based extraction method, an ultrasonic extraction method, and a supercritical-fluid-based extraction method.

BRIEF DESCRIPTION OF THE SEVERAL VIEWS OF THE DRAWINGS

The foregoing features and advantages of the present invention can be better understood by referring to the following detailed description of some embodiments of the invention in conjunction with the accompanying drawings, in which.

DETAILED DESCRIPTION OF THE INVENTION

With a view to cleaning the skin, preventing excessive cleaning, and carrying out preliminary skin care to enhance skin functions, the present invention provides a mild cleansing composition nearly saturated, saturated, or supersaturated with an active ingredient. The composition includes one or more than one active ingredient and one or more than one surfactant. The composition of the invention may further include an appropriate amount of water. The composition of the invention may further include an appropriate amount of cosmetic excipient.

Figure 1:
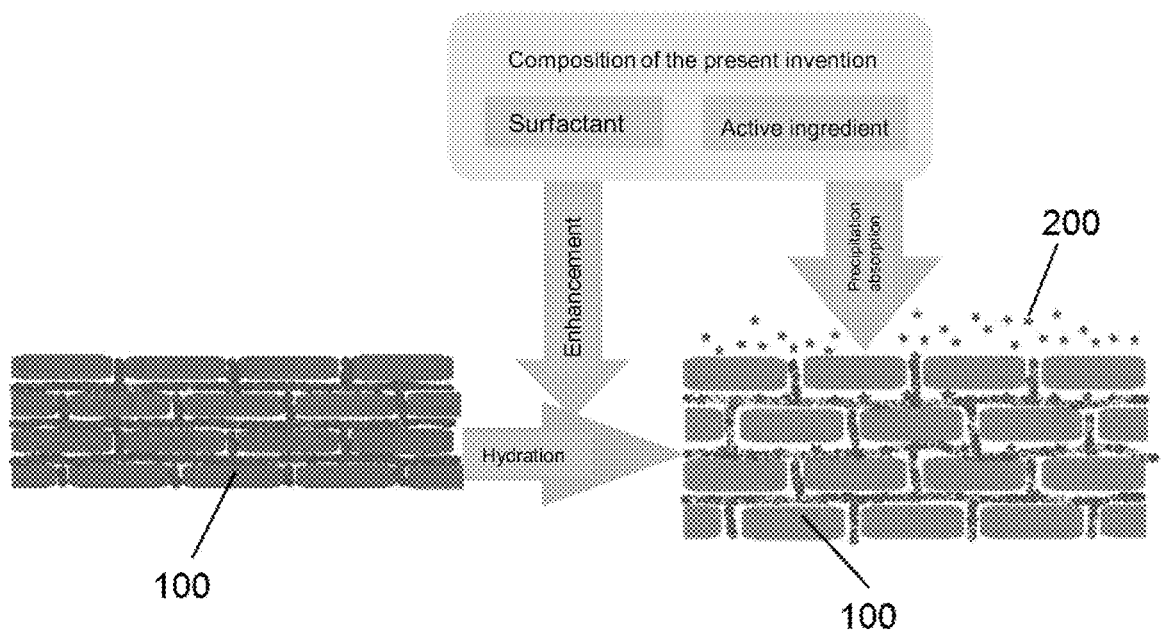
FIG. 1 schematically shows how the invention uses a surfactant and water to hydrate the stratum corneum and how the absorption of an active ingredient by the skin is facilitated by the active ingredient being present at a concentration near saturation, of saturation, or of supersaturation.

Please refer to FIG. 1, which shows how the invention uses a surfactant and water to hydrate the stratum corneum 100 and how the precipitation of an active ingredient 200 on the stratum corneum, and hence the absorption of the active ingredient by the skin, are facilitated by the active ingredient being present at a concentration near saturation, of saturation, or of supersaturation.

The following embodiments are used to demonstrate the present invention. Those embodiments, however, are by no means intended to be restrictive of the scope of the invention and serve only to indicate how to implement the materials and method of the invention.

The "at least one surfactant" referred to in the embodiments of the present invention is one or an arbitrary combination of a long-chain betaine, sodium lauroyl sarcosinate, sodium lauroyl methyl isethionate, and potassium cocoyl glycinate.

The "at least one active ingredient" referred to in the embodiments of the present invention is an extract (or extracts) of one or an arbitrary combination of *Angelica dahurica*, *Ampelopsis japonica*, *Atractylodes macrocephala*, *Bletilla striata*, *Wolfiporia extensa*, *Aconitum carmichaelii*, and *Lithospermum erythrorhizon*.

Figure 2:
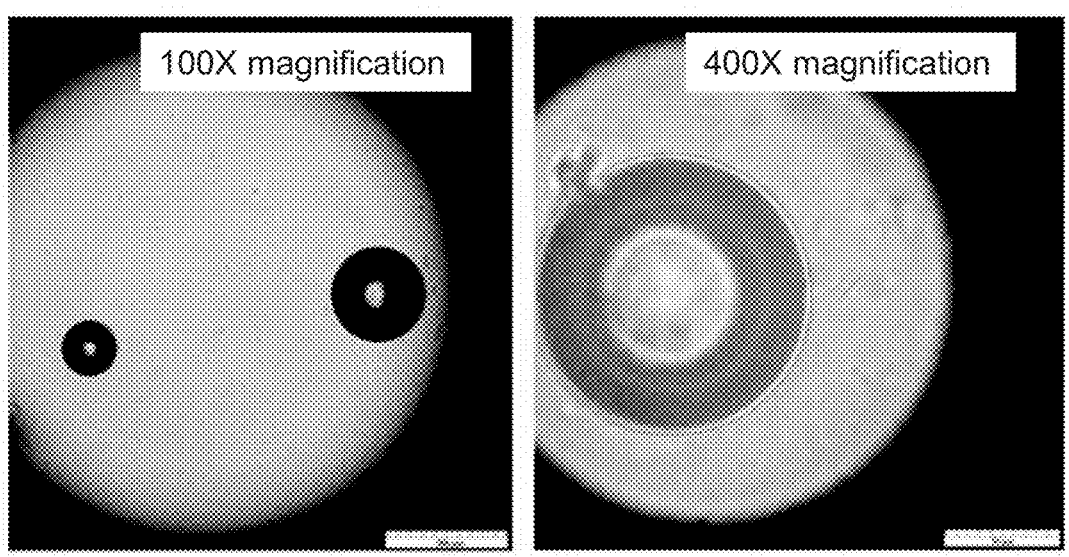
FIG. 2 is a series of micrographs of different magnification ratios, showing the composition of the invention in different dosage forms.
Figure 3:
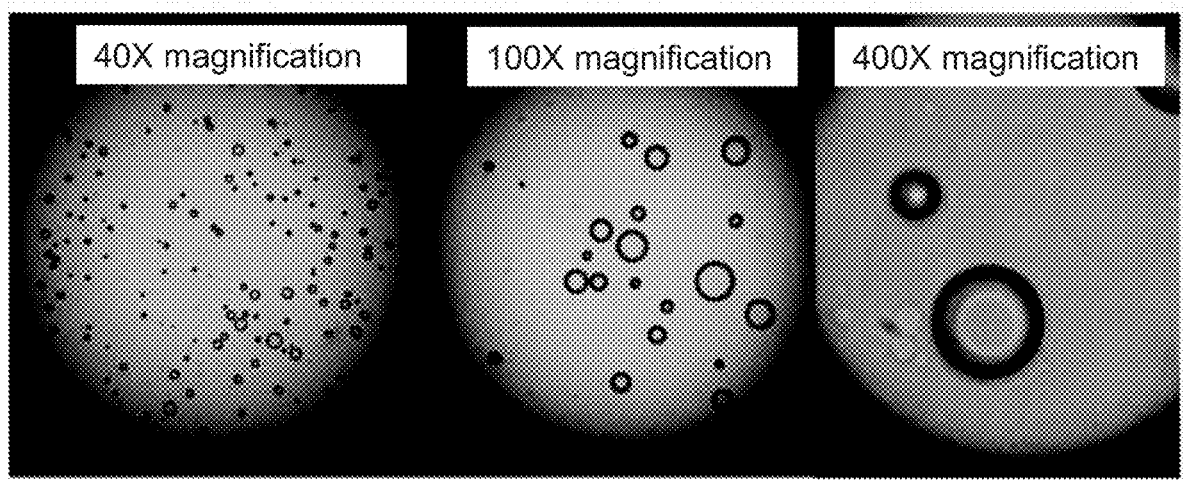
FIG. 3 is a series of micrographs of different magnification ratios, showing how the composition in embodiment 12 of the invention precipitates before being mixed with water.
Figure 4:
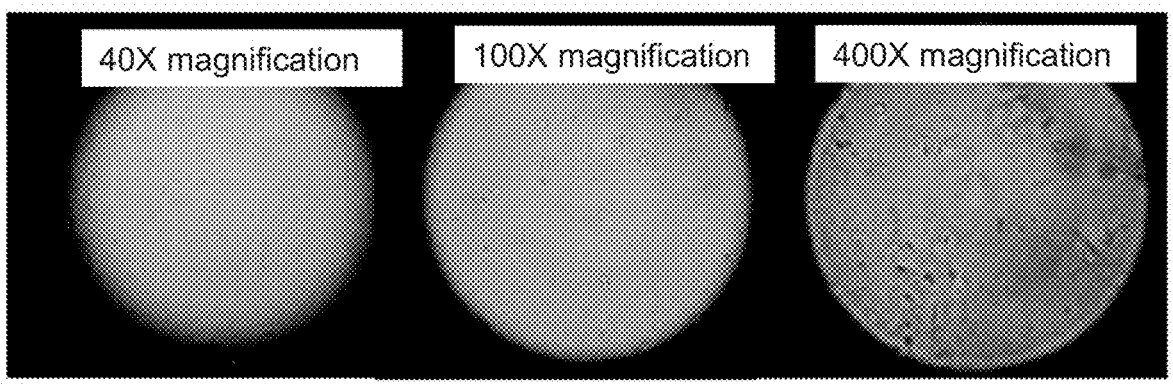
FIG. 4 is a series of micrographs of different magnification ratios, showing how the composition in embodiment 12 of the invention precipitates at a 10-minute time point after being thoroughly mixed with water in a weight ratio of 1:1.
Figure 5:
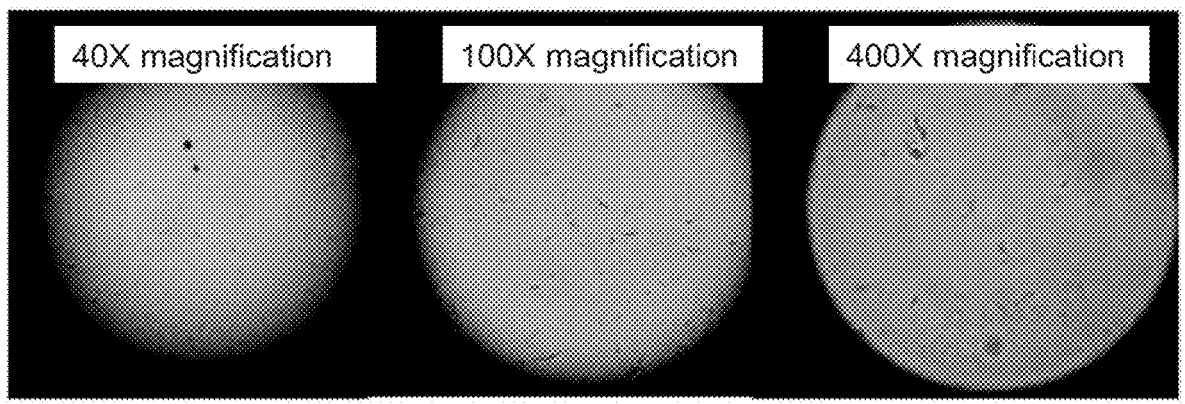
FIG. 5 is a series of micrographs of different magnification ratios, showing how the composition in embodiment 12 of the invention precipitates at a 60-minute time point after being thoroughly mixed with water in a weight ratio of 1:1.
Figure 6:
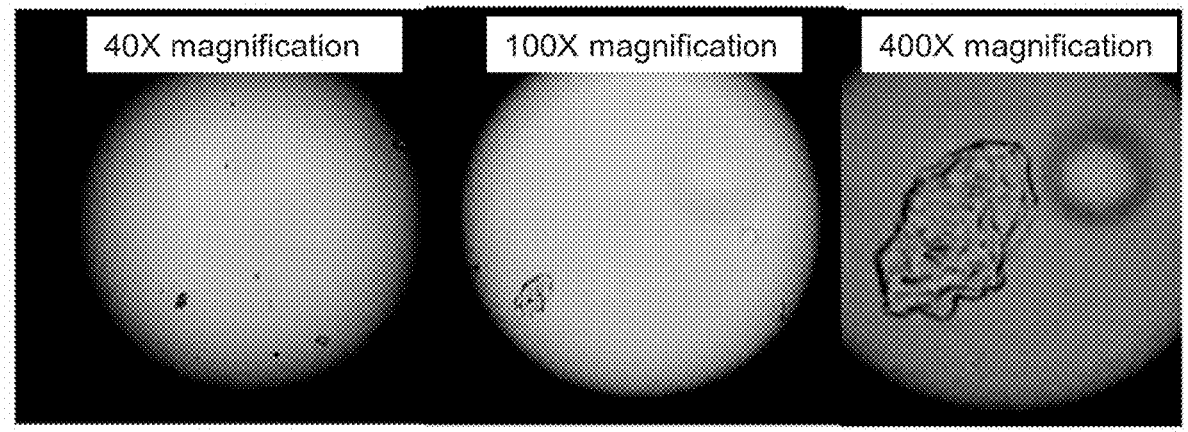
FIG. 6 is a series of micrographs of different magnification ratios, showing how the composition in embodiment 12 of the invention precipitates at a 360-minute time point after being thoroughly mixed with water in a weight ratio of 1:1.

As shown in FIG. 2, an embodiment of the present invention may be in the dosage form of an O/W microemulsion (American Journal of Pharmtech Research, 2012), an emulsion, or a micelle solution (Cancers, July 2018), depending on the formula of the composition.

Embodiment 1: Active-Ingredient-Containing Mild Cleansing Composition of Formula 1 and Method for Making the Same In this embodiment, the final product, each 1000 g of which contained about 5 g of active ingredients, was made by the following method. Each active ingredient was extracted with a mixed extraction liquid prepared by mixing equal amounts by weight of alcohol and water. The weight ratio of the mixed extraction liquid to the raw material of each active ingredient was 10:1 to 50:1. The extraction temperature was 50 to 100° C., and the duration of the extraction process was 1 to 10 hours. The extraction products were 1000 mg of *Angelica dahurica* extract, 1000 mg of *Ampelopsis japonica* extract, 1000 mg of *Atractylodes macrocephala* extract, 500 mg of *Bletilla striata* extract, 500 mg of *Wolfiporia extensa* extract, 500 mg of *Aconitum carmichaelii* extract, and 500 mg of *Lithospermum erythrorhizon* extract. The extracts were then mixed with 50 g of cocamidopropyl betaine, 50 g of sodium lauroyl sarcosinate, 50 g of sodium lauroyl methyl isethionate, 50 g of potassium cocoyl glycinate, and an appropriate amount of water. The mixture was heated (when necessary) until homogeneous, then added with 10 g of PEG-7 glyceryl cocoate and 10 g of PEG-200 hydrogenated glyceryl palmate, mixed well, then added with 10 g of sodium chloride, stirred until thoroughly mixed, and allowed to cool down to room temperature. Table 1 shows the formula of the composition in embodiment 1.

TABLE 1

Formula of the composition in embodiment 1

| Ingredient | Function | Percentage by weight | Extraction method |
|---|---|---|---|
| Angelica dahurica | Active ingredient | 0.10% | Alcohol and water |
| Ampelopsis japonica | Active ingredient | 0.10% | Alcohol and water |
| Atractylodes macrocephala | Active ingredient | 0.10% | Alcohol and water |
| Bletilla striata | Active ingredient | 0.05% | Alcohol and water |
| Wolfiporia extensa | Active ingredient | 0.05% | Alcohol and water |
| Aconitum carmichaelii | Active ingredient | 0.05% | Alcohol and water |
| Lithospermum erythrorhizon | Active ingredient | 0.05% | Alcohol and water |
| Alkyl amido betaine | Surfactant | 5.00% | — |
| Sodium lauroyl sarcosinate | Surfactant | 5.00% | — |
| Sodium lauroyl methyl isethionate | Surfactant | 5.00% | — |
| Potassium cocoyl glycinate | Surfactant | 5.00% | — |
| PEG-7 glyceryl cocoate | Thickening agent | 1.00% | — |
| PEG-200 hydrogenated glyceryl palmate | Thickening agent | 1.00% | — |
| Sodium chloride | Viscosity modifier | 1.00% | — |
| Pure water | Carrier, thinner | q.s. | — |

Embodiments 2 to 12

Active-ingredient-containing mild cleansing compositions of formulae 2 to 12 were made by a method similar to that of embodiment 1, with the ingredients of each of formulae 2 to 12 and the corresponding extraction methods shown in Table 2 to 3. Please refer to Table 2 for the formulae of the compositions in embodiments 1 to 12, Table 3 for the extraction methods of the active ingredients in the compositions in embodiments 1 to 12, and Table 4 for the extraction conditions of each of those extraction methods.

TABLE 2

Formulae of the compositions in embodiments 1 to 12

| Ingredient | Formula | | | | | |
|---|---|---|---|---|---|---|
| | 1 | 2 | 3 | 4 | 5 | 6 |
| | Percentage by weight | | | | | |
| Angelica dahurica | 0.10% | 0.20% | 0.30% | 0.40% | — | 0.20% |
| Ampelopsis japonica | 0.10% | 0.20% | 0.30% | 0.40% | — | 0.20% |
| Atractylodes macrocephala | 0.10% | 0.20% | 0.30% | 0.40% | 0.10% | — |
| Bletilla striata | 0.05% | 0.10% | 0.20% | 0.30% | 0.10% | — |
| Wolfiporia extensa | 0.05% | 0.10% | 0.20% | 0.30% | 0.10% | 0.20% |
| Aconitum carmichaelii | 0.05% | 0.10% | 0.20% | — | 0.10% | 0.20% |
| Lithospermum erythrorhizon | 0.05% | 0.10% | — | 0.20% | 0.10% | 0.20% |
| Alkyl amido betaine | 5.00% | 10.0% | 10.0% | 15.0% | 20.0% | — |
| Sodium lauroyl sarcosinate | 5.00% | 5.00% | 10.0% | 10.0% | — | 20.0% |
| Sodium lauroyl methyl isethionate | 5.00% | 10.0% | 10.0% | 15.0% | 20.0% | — |
| Potassium cocoyl glycinate | 5.00% | 5.00% | 10.0% | 10.0% | — | 20.0% |
| Disodium laureth sulfosuccinate | — | — | — | — | — | — |
| PEG-40 hydrogenated castor oil | — | — | — | — | — | — |
| PEG-7 glyceryl cocoate | 1.00% | 0.50% | 0.50% | — | 1.00% | — |
| PEG-200 hydrogenated glyceryl palmate | 1.00% | 0.50% | 0.50% | — | 1.00% | — |
| Sodium chloride | 1.00% | 2.00% | 1.00% | — | 2.00% | — |
| EDTA disodium salt | — | — | — | 0.50% | — | — |
| Chlorphenesin | — | — | 0.10% | — | — | — |
| Benzyl alcohol | — | — | — | 0.20% | — | — |
| Lavender | — | — | — | — | — | 0.10% |
| Pure water | q.s. | q.s. | q.s. | q.s. | q.s. | q.s. |

| Ingredient | Formula | | | | | |
|---|---|---|---|---|---|---|
| | 7 | 8 | 9 | 10 | 11 | 12 |
| | Percentage by weight | | | | | |
| Angelica dahurica | 0.30% | 0.60% | — | 1.00% | 1.20% | 1.80% |
| Ampelopsis japonica | 0.30% | — | 1.20% | 1.00% | 1.20% | 1.80% |
| Atractylodes macrocephala | 0.40% | 0.60% | — | 0.80% | 1.20% | 1.80% |
| Bletilla striata | 0.40% | — | 1.20% | 0.40% | 0.80% | 0.80% |
| Wolfiporia extensa | — | 0.60% | — | 0.80% | 0.70% | 0.80% |
| Aconitum carmichaelii | — | — | 0.60% | — | 0.80% | 0.80% |
| Lithospermum erythrorhizon | 0.10% | 0.20% | — | — | 0.10% | 0.20% |
| Alkyl amido betaine | 15.0% | 5.00% | 10.0% | 10.0% | 15.0% | 15.0% |
| Sodium lauroyl sarcosinate | 10.0% | 15.0% | 10.0% | 10.0% | 10.0% | 10.0% |
| Sodium lauroyl methyl isethionate | 15.0% | 5.00% | 10.0% | 10.0% | 15.0% | 15.0% |
| Potassium cocoyl glycinate | 10.0% | 15.0% | 10.0% | 10.0% | 10.0% | 10.0% |

TABLE 2-continued

Formulae of the compositions in embodiments 1 to 12

| | 1 | 2 | 3 | 4 | 5 | 6 |
|---|---|---|---|---|---|---|
| Disodium laureth sulfosuccinate | — | — | 1.00% | 2.00% | 3.00% | 4.00% |
| PEG-40 hydrogenated castor oil | — | 0.50% | 1.00% | 2.00% | 3.00% | 4.00% |
| PEG-7 glyceryl cocoate | 0.50% | — | 0.50% | 0.20% | 0.05% | — |
| PEG-200 hydrogenated glyceryl palmate | 0.50% | — | — | 0.10% | 0.05% | — |
| Sodium chloride | 1.00% | — | 0.50% | 0.30% | 0.10% | — |
| EDTA disodium salt | — | — | — | — | — | — |
| Chlorphenesin | — | — | — | — | — | — |
| Benzyl alcohol | — | — | — | — | — | — |
| Lavender | — | 0.10% | — | — | — | — |
| Pure water | q.s. | q.s. | q.s. | q.s. | q.s. | q.s. |

TABLE 3

Extraction methods of the active ingredients in the compositions in embodiments 1 to 12

| | Formula | | | | | | | | | | | |
|---|---|---|---|---|---|---|---|---|---|---|---|---|
| Ingredient | 1 | 2 | 3 | 4 | 5 | 6 | 7 | 8 | 9 | 10 | 11 | 12 |
| | Extraction method | | | | | | | | | | | |
| *Angelica dahurica* | Alcohol and water | Super-critical | Alcohol | Ultra-sonic | — | Alcohol and water | Ultra-sonic | Alcohol | — | Alcohol and water | Water | Ultra-sonic |
| *Ampelopsis japonica* | Alcohol and water | Water | Water | Ultra-sonic | — | Alcohol and water | Ultra-sonic | — | Water | Alcohol and water | Water | Water |
| *Atractylodes macrocephala* | Alcohol and water | Water | Water | Ultra-sonic | Water | — | Ultra-sonic | Alcohol | — | Alcohol and water | Water | Water |
| *Bletilla striata* | Alcohol and water | Water | Water | Ultra-sonic | Water | — | Ultra-sonic | — | Water | Alcohol and water | Water | Water |
| *Wolfiporia extensa* | Alcohol and water | Alcohol | Alcohol | Ultra-sonic | Water | Alcohol | — | Alcohol | — | Alcohol and water | Water | Super-critical |
| *Aconitum carmichaelii* | Alcohol and water | Alcohol | Alcohol | — | Water | Alcohol | — | — | Water | — | Water | Ultra-sonic |
| *Lithospermum erythrorhizon* | Alcohol and water | Super-critical | — | Super-critical | Alcohol | Alcohol | Alcohol | Super-critical | — | — | Alcohol | Super-critical |

TABLE 4

Extraction conditions of each extraction method

| Method | Composition of extraction solvent | Weight ratio of raw material to solvent | Extraction temperature (° C.) | Extraction time (hour) | Drying method |
|---|---|---|---|---|---|
| Water-based extraction | 100% pure water | 1:10 to 1:50 | 35 to 100 | 1 to 10 | Vacuum-concentration hypobaric drying or freeze-drying |
| Alcohol-based extraction | 100% alcohol | 1:10 to 1:50 | 35 to 55 | 1 to 10 | Vacuum-concentration hypobaric drying or freeze-drying |
| Alcohol-and-water-based extraction | Mixed solution of alcohol and water (in a weight ratio of 1:5 to 5:1) | 1:10 to 1:50 | 50 to 100 | 1 to 10 | Vacuum-concentration hypobaric drying or freeze-drying |

TABLE 4-continued

Extraction conditions of each extraction method

| Method | Composition of extraction solvent | Weight ratio of raw material to solvent | Extraction temperature (° C.) | Extraction time (hour) | Drying method |
|---|---|---|---|---|---|
| Ultrasonic extraction | Mixed solution of alcohol and water (in a weight ratio of 1:5 to 5:1) | 1:10 to 1:50 | 35 to 55 | 1 to 10 | Vacuum-concentration hypobaric drying or freeze-drying |
| Supercritical extraction | Supercritical carbon dioxide at 250 to 350 bar | NA | 35 to 45 | 1 to 10 | NA |

A series of tests were performed on the mild cleansing composition nearly saturated, saturated, or supersaturated with an active ingredient according to the present invention, and the test results are as follows.

[Experiments with Regard to Near-Saturation, Saturation, and Supersaturation]

Figure 7:
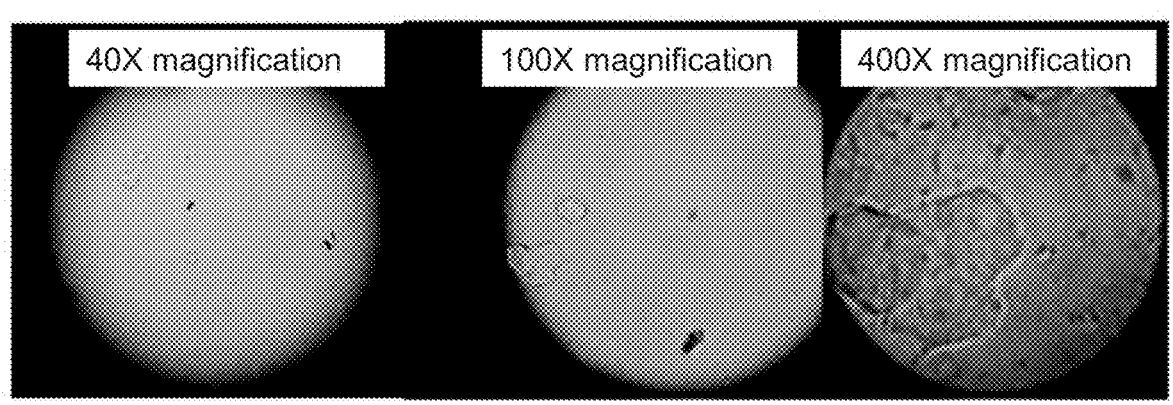
FIG. 7 is a series of micrographs of different magnification ratios, showing how the composition in embodiment 12 of the invention precipitates at a 720-minute time point after being thoroughly mixed with water in a weight ratio of 1:1.
Figure 8:
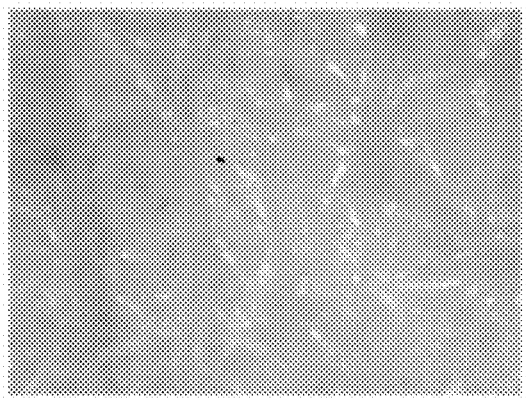
FIG. 8 is a 200× micrograph showing the state of a test subject's skin before the skin is washed with a common cleaning product.
Figure 9:
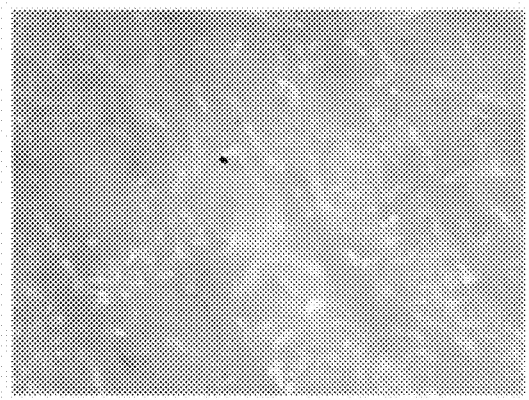
FIG. 9 is a 200× micrograph showing the state of the test subject's skin before the skin is washed with the composition in embodiment 10 of the invention.
Figure 10:
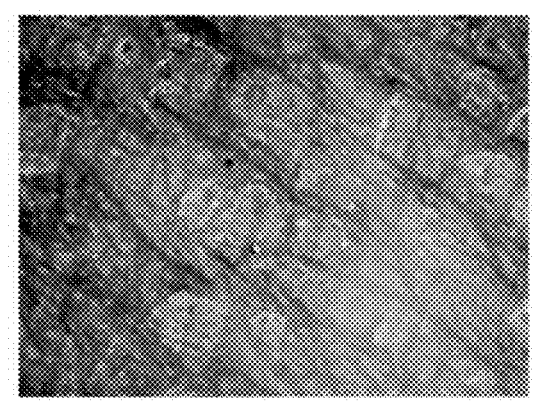
FIG. 10 is a 30× micrograph showing the state of the test subject's skin after the skin is washed with the common cleaning product for 20 times continuously.
Figure 11:
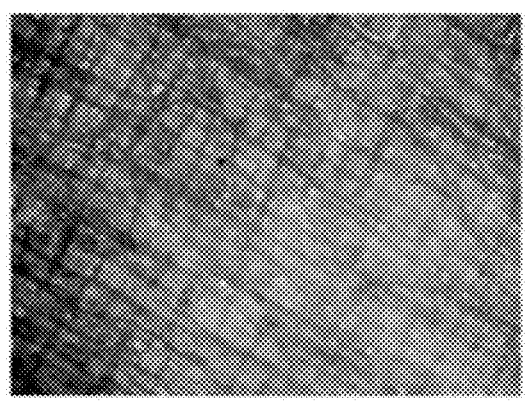
FIG. 11 is a 30× micrograph showing the state of the test subject's skin after the skin is washed with the composition in embodiment 10 of the invention for 20 times continuously.
Figure 12:
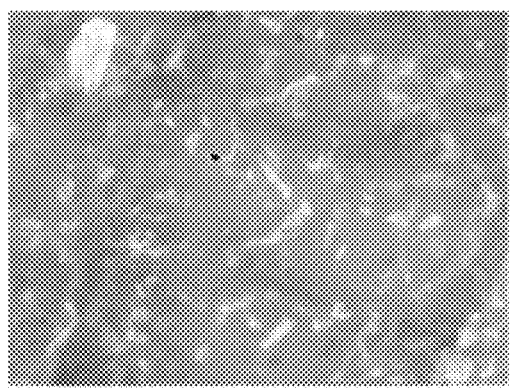
FIG. 12 is a 200× micrograph showing the state of the test subject's skin after the skin is washed with the common cleaning product for 20 times continuously.
Figure 13:
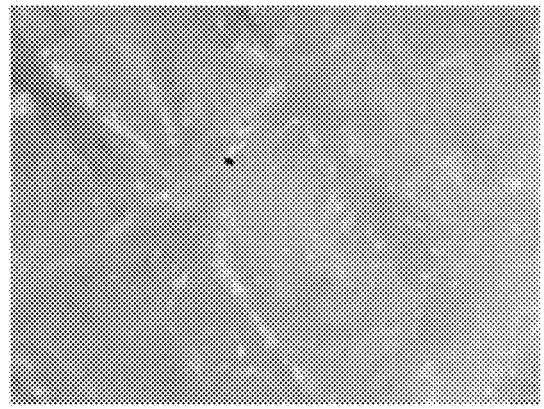
FIG. 13 is a 200× micrograph showing the state of the test subject's skin after the skin is washed with the composition in embodiment 10 of the invention for 20 times continuously.

Microscopic observation was carried out as follows. First, the composition in embodiment 12 of the present invention was observed under a microscope as it was. Second, the composition in embodiment 12 of the invention was thoroughly mixed with water in a weight ratio of 1:1 and then observed under the microscope at a 10-minute, 60-minute, 360-minute, and 720-minute time point. The microscopic observation was intended to find out whether and when the composition precipitated as a result of saturation. The observation results in FIG. 3 to FIG. 7 show that the composition of the invention did not precipitate when not mixed with water (FIG. 3), that the mixture of the composition of the invention and water in a weight ratio of 1:1 produced at the 10-minute time point a minute amount of precipitate that was visible under an optical microscope (FIG. 4), that the mixture produced a small amount of precipitate at the 60-minute time point (FIG. 5), that the mixture produced a coagulated precipitate at the 360-minute time point (FIG. 6), and that the mixture produced a large amount of precipitate at the 720-minute time point (FIG. 7). (Had the experiments been carried out macroscopically, a critical-saturation experiment would have been conducted through a stability test because coagulation would have taken place gradually over the course of long-term storage at rest due to a reduction in energy.) The experimental results show that the composition of the invention has the outstanding design of being near the saturation threshold (Journal of Pharmaceutical Sciences, January 2012), and this proves that the composition of the invention was based on the concept of "quality by design" so as to provide skin care as well as protection for the skin when actually used to clean the skin.

[Experiments with Regard to the Prevention of Excessive Cleaning and to Protection]

An inner-side surface portion of a test subject's thigh was subjected to 20 continuous cleaning cycles each including washing the inner-side surface portion with a commercially available cleaning product (Dermisa Brightening Bar) and then wiping the inner-side surface portion dry. Another 20 continuous cleaning cycles were performed on a different inner-side surface portion of the thigh in the same way except that the composition in embodiment 10 of the present invention was used in place of the commercially available cleaning product. The experimental results regarding the prevention of excessive cleaning are shown in Table 5 and FIG. 8 to FIG. 13.

TABLE 5

Experimental results regarding the prevention of excessive cleaning

| | Item | Common cleaning product | Composition of the present invention | Magnification ratio |
|---|---|---|---|---|
| Before cleaning | Degree of radiance | 1.4 GU | 1.4 GU | |
| | Microscopic observation | Smooth (FIG. 8) | Smooth (FIG. 9) | 200× |
| After 20 cleaning cycles | Degree of radiance | 1.2 GU | 1.6 GU | |
| | Microscopic observation | Stratum corneum damage (FIG. 10) | Smooth (FIG. 11) | 30× |
| | Microscopic observation | Stratum corneum damage (FIG. 12) | Smooth (FIG. 13) | 200× |

The experiments included evaluation of the degree of radiance and microscopic observation, in addition to the aforesaid cleaning cycles, which were carried out by simulating a common washing process. The experimental results show that washing repeatedly with the common cleaning product within a short time caused damage to the skin surface. More specifically, stratum corneum damage and white detached (or even curled) skin flakes were visible under the microscope, and the microscopic observation results were echoed macroscopically by a reduction in the degree of radiance. By contrast, washing repeatedly with the composition of the present invention within a short time not only caused no damage to the skin surface (as can be known by the fact that the microscopic observation results show no difference between the unwashed skin and the washed skin), but also enhanced the delicacy and smoothness of the skin (as revealed by the evaluation results of the degree of radiance). It can be expected, therefore, that long-term use of the composition of the invention will further enhance the delicacy and smoothness of skin and thereby increase the degree of radiance so significantly that the difference is visible to the naked eye.

According to the above, and as is consistent with general knowledge and common sense, washing the skin with a conventional cleaning product tends to damage the stratum corneum and roughen the skin surface, making it necessary to apply a skin care product (e.g., a cream) to the damaged skin. The composition of the present invention, on the other hand, is so designed that its at least one active ingredient is present at a concentration near saturation, of saturation, or of supersaturation and therefore can be precipitated during the skin cleaning process and absorbed by the skin to protect the skin from damage.

[Experiments with Regard to the Degree of Moisture Retention]

Figure 14:
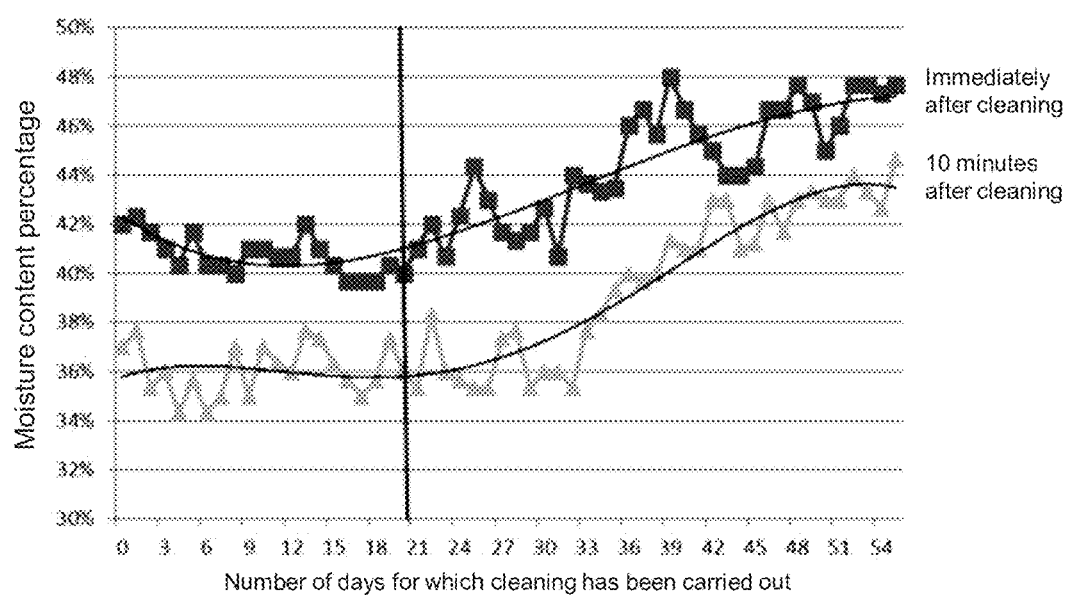
FIG. 14 is a plot showing the test results of the degree of moisture retention, or more particularly the degrees of moisture retention of the test subject's skin immediately after and 10 minutes after the skin is washed with the composition in embodiment 11 of the invention.

The test subject's face was subjected to a standard cleaning operation that included washing the face with one of a common face cleaning product (Dermis a Brightening Bar) and the composition in embodiment 11 to remove dirt from the face and washing the face again with the one of the common face cleaning product and the composition in embodiment 11 for cleaning and skin care purposes. After each standard cleaning operation, the skin was tested with a commercially available skin testing instrument (RUNVE Skin Analyzer), which can measure three parameters: moisture content, oil content, and delicacy/roughness (the latter two of which can be used in conjunction with evaluation of the degree of radiance). The moisture content measurement was the average of the measurements taken respectively at three different points on the face (the forehead and the cheek bones). Washing with the common face cleaning product and testing after each standard cleaning operation continued for about three weeks. Following that, cleaning with the composition of the present invention and testing after each standard cleaning operation continued for more than four weeks. As can be seen in the plot showing the test results of the degree of moisture retention (FIG. 14), the indicator of the degree of moisture detention, whether measured immediately after cleaning or measured 10 minutes after cleaning, was greatly improved after the composition of the invention was used for two weeks.

When the common face cleaning product was used, the degree of moisture retention measured immediately after cleaning ranged approximately between 40 and 42, and the degree of moisture retention measured when the face was dry ranged approximately between 34 and 38; therefore, it can be known from Table 6, which shows the degrees of moisture retention as classified according to the user manual of the skin testing instrument, that the test subject's skin was normally hydrated immediately after cleaning and was dry after 10 minutes of moisture evaporation. After the composition of the present invention was used for about two weeks, however, the degree of moisture retention measured immediately after cleaning ranged approximately between 43 and 48, and the degree of moisture retention measured when the face was dry ranged approximately between 38 and 44; therefore, according to the classification of the degrees of moisture retention set forth in the user manual of the skin testing instrument, the test subject's skin was well hydrated immediately after cleaning and was normally hydrated after 10 minutes of moisture evaporation.

TABLE 6

Classification of the degrees of moisture retention

| | The number of columns displayed | | | | |
|---|---|---|---|---|---|
| | 1 | 2 | 3 | 4 | 5 |
| Moisture content percentage | ≤33% | 34%-37% | 38%-42% | 43%-46% | ≥47% |
| Degree of moisture retention | Low (dry skin) | Slightly low (slightly dry skin) | Normal (normally hydrated skin) | High (well hydrated skin) | Extremely high (extremely highly hydrated skin) |

[Experiments with Regard to the Degree of Radiance]

Generally, based on a dermatologist's understanding of the degree of radiance of the skin, the sebum secreted by the sebaceous glands and certain substances in the environment will attach to the skin, causing an increase in the degree of radiance of the skin (Biomedical Optics Express). Such an environment on the skin, however, tends to give rise to acne, seborrheic dermatitis, or other skin diseases. If the skin has been cleaned and rid of excessive sebum but still has a noticeable degree of radiance, the radiance can be attributed to sustained good health of the skin, which is typically accompanied by, for example, a reduction in skin roughness (Skin Research and Technology), a reduction of wrinkles, a relatively high degree of moisture retention, and delicacy of the skin, all of which can be promoted by, for example, proliferation of the epidermal growth factor or collagen (WO2005037270A1). The composition of the present invention is rich in active ingredients and therefore sufficient to enhance skin health, thereby reducing wrinkles and increasing the degree of radiance of cleaned skin (International Journal of Research in Pharmacy and Chemistry).

Figure 15:
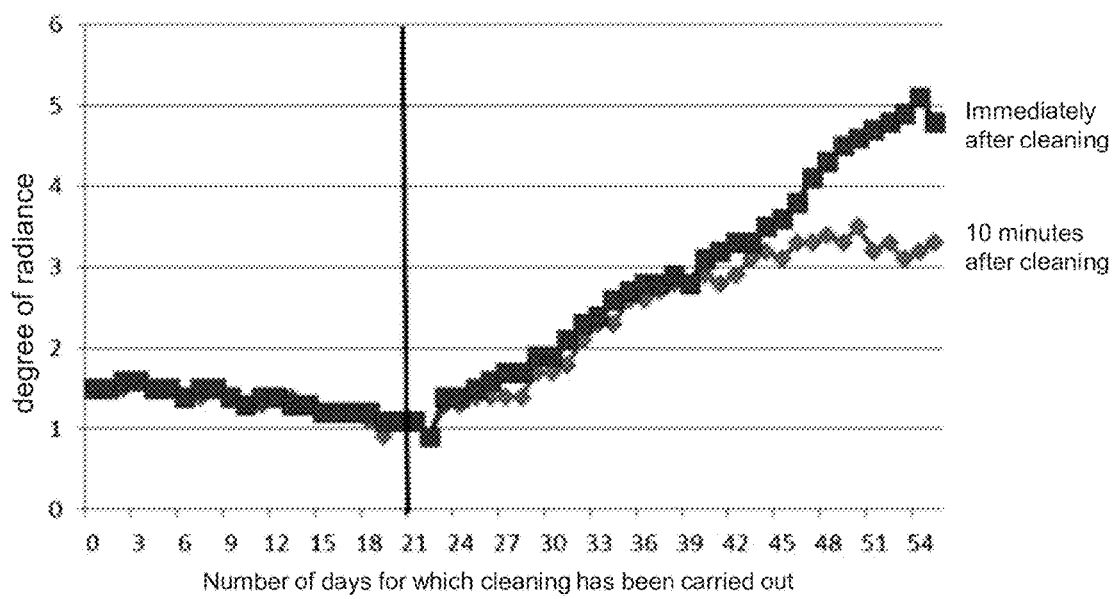
FIG. 15 is a plot showing the test results of the degree of radiance, or more particularly the degrees of radiance of the test subject's skin immediately after and 10 minutes after the skin is washed with the composition in embodiment 11 of the invention.

The test subject's face was subjected to a standard cleaning operation that included washing the face with one of a common face cleaning product (Dermisa Brightening Bar) and the composition of the present invention to remove dirt from the face and washing the face again with the one of the common face cleaning product and the composition of the present invention for cleaning and skin care purposes. Each day after the standard cleaning operation, the degree of radiance of the flattest area of the face, i.e., the forehead, was tested with a commercially available radiance testing instrument (BYK Micro-Gloss). Washing with the common face cleaning product and testing after each standard cleaning operation continued for about three weeks. Following that, cleaning with the composition of the invention and testing after each standard cleaning operation continued for more than four weeks. As can be seen in the plot showing the test results of the degree of radiance (FIG. 15), the indicator of the degree of radiance, whether measured immediately after cleaning or measured 10 minutes after cleaning, was greatly improved after the composition of the invention was used for two weeks.

The degree of radiance of a human face with sebum is generally about 2 GU (gloss unit), may be reduced to about 1 GU after the face is cleaned or when skin roughness is increased, and may be raised to about 2.5 GU when the delicacy of the skin is increased or after a skin care or cosmetic product is used (Optical Review). Prolonged use of the composition of the present invention increased the degree of radiance to about 3 GU to 5 GU before any skin care product was used, and the difference in the degree of radiance was visible to the human eye (a difference identifiable with the human eye is about 3 GU); in other words, a general user will be able to see the increased degree of radiance and clearly feel the delicacy of their skin. The degree of radiance measured immediately after cleaning was about 3 GU because the hydrated skin was not yet dry and the stratum corneum had not returned to its original state. After 10 minutes, however, the degree of radiance was restored to about 5 GU.

Figure 16:
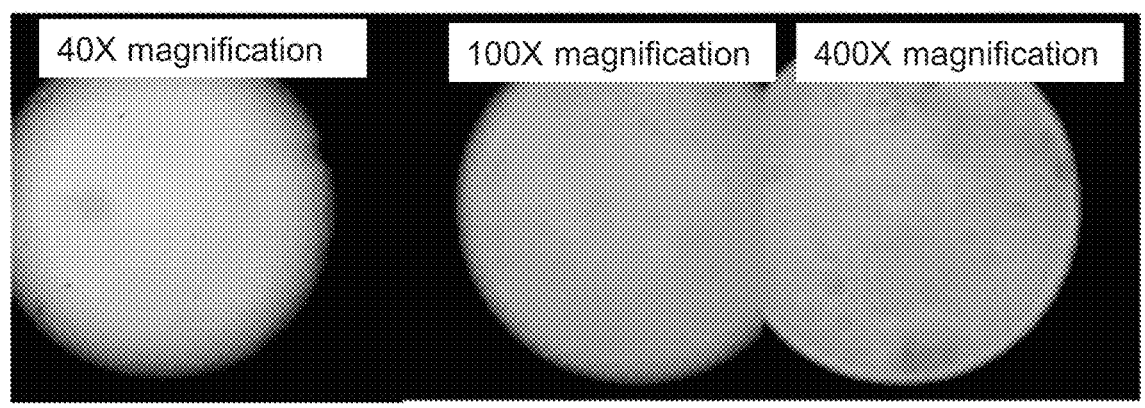
FIG. 16 is a series of micrographs of different magnification ratios, showing how the composition in comparative embodiment 13 precipitates at a 10-minute time point after being thoroughly mixed with water in a weight ratio of 1:1.
Figure 17:
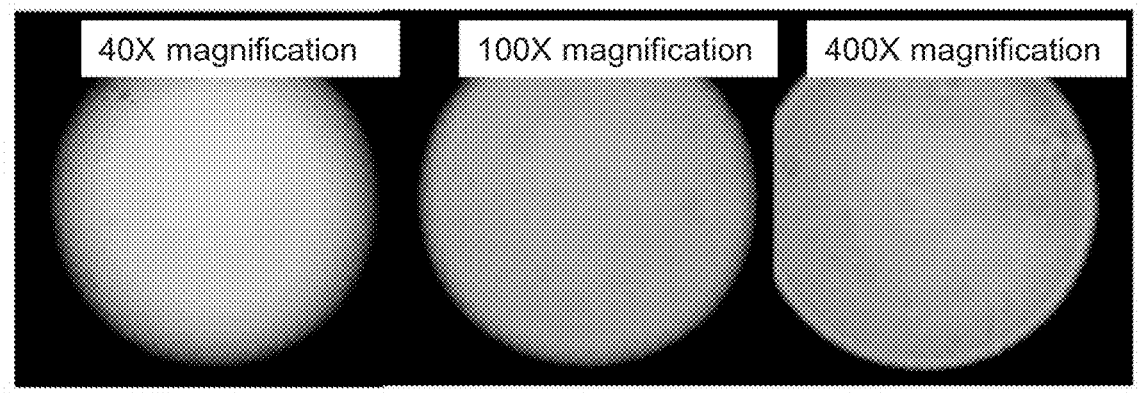
FIG. 17 is a series of micrographs of different magnification ratios, showing how the composition in comparative embodiment 13 precipitates at a 60-minute time point after being thoroughly mixed with water in a weight ratio of 1:1.
Figure 18:
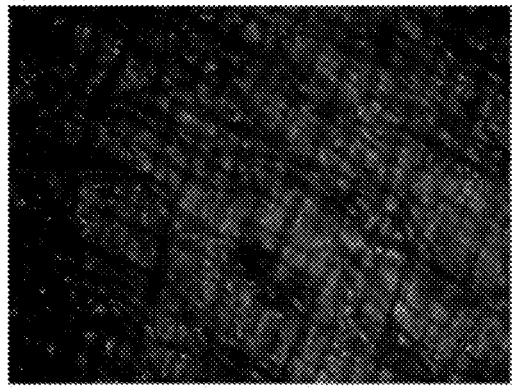
FIG. 18 is a 30× micrograph showing the state of the test subject's skin before the skin is washed with the composition in comparative embodiment 13.
Figure 19:
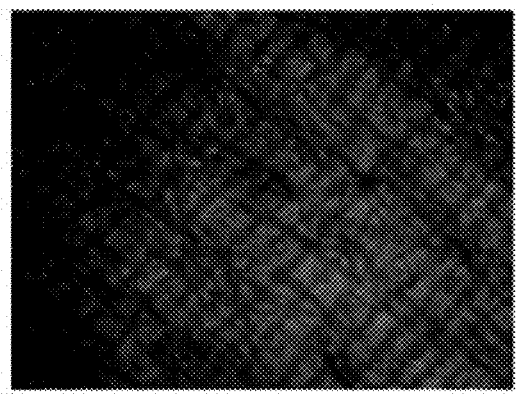
FIG. 19 is a 30× micrograph showing the state of the test subject's skin after the skin is washed with the composition in comparative embodiment 13 for 20 times continuously.
Figure 20:
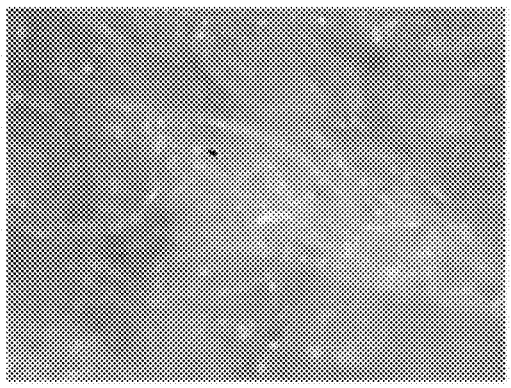
FIG. 20 is a 200× micrograph showing the state of the test subject's skin before the skin is washed with the composition in comparative embodiment 13.
Figure 21:
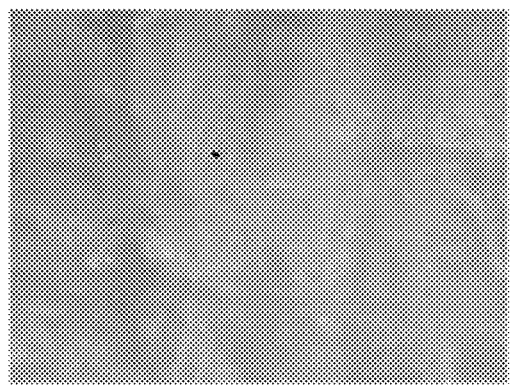
FIG. 21 is a 200× micrograph showing the state of the test subject's skin after the skin is washed with the composition in comparative embodiment 13 for 20 times continuously.

Comparative Embodiment 13: Mild Cleansing Composition of Formula 13 with Active Ingredients at Concentrations Below Saturation and Method for Making the Same In this comparative embodiment, the final product, each 1000 g of which contained about 0.83 g of active ingredients, was made by the following method. Each active ingredient was extracted with a mixed extraction liquid prepared by mixing equal amounts by weight of alcohol and water. The extraction products were 100 mg of *Angelica dahurica* extract, 100 mg of *Ampelopsis japonica* extract, 100 mg of *Atractylodes macrocephala* extract, 50 mg of *Bletilla striata* extract, 50 mg of *Wolfiporia extensa* extract, 50 mg of *Aconitum carmichaelii* extract, and 50 mg of *Lithospermum erythrorhizon* extract. The extracts were then mixed with 50 g of cocamidopropyl betaine, 50 g of sodium lauroyl sarcosinate, 50 g of sodium lauroyl methyl isethionate, 50 g of potassium cocoyl glycinate, and an appropriate amount of water. The mixture was heated (when necessary) until homogeneous, then added with 10 g of PEG-7 glyceryl cocoate, 10 g of PEG-200 hydrogenated glyceryl palmate, and 10 g of sodium chloride, stirred until thoroughly mixed, and allowed to cool down to room temperature. Table 7 shows the formula of the composition in comparative embodiment 13.

in order to find out whether the unsaturated composition precipitated. The observation results in FIG. 16 and FIG. 17 show that the unsaturated composition in comparative embodiment 13 did not precipitate.

[Experiments with Regard to the Prevention of Excessive Cleaning and to Protection]

An inner-side surface portion of the test subject's thigh was subjected to 20 continuous cleaning cycles each including washing the inner-side surface portion with the composition in comparative embodiment 13 and then wiping the inner-side surface portion dry. The experimental results regarding the prevention of excessive cleaning are shown in Table 8 and FIG. 18 to FIG. 21.

TABLE 8

Experimental results regarding the prevention of excessive cleaning

| Item | | Unsaturated embodiment 13 | Magnification ratio |
|---|---|---|---|
| Before cleaning | Degree of radiance | 1.4 GU | |
| | Microscopic observation | Generally smooth (FIG. 18) | 30× |
| | Microscopic observation | Smooth (FIG 20) | 200× |
| After 20 cleaning cycles | Degree of radiance | 1.4 GU | |
| | Microscopic observation | Generally smooth (FIG. 19) | 30× |
| | Microscopic observation | Generally smooth (FIG. 21) | 200× |

The experiments included evaluation of the degree of radiance and microscopic observation, in addition to the aforesaid cleaning cycles, which were carried out by simulating a common washing process. The experimental results reveal that the skin surface did not show any significant

TABLE 7

Formula of the composition in comparative embodiment 13

| Ingredient | Function | Percentage by weight | Extraction method |
|---|---|---|---|
| *Angelica dahurica* | Active ingredient | 0.01% | Alcohol and water |
| *Ampelopsis japonica* | Active ingredient | 0.003% | Alcohol and water |
| *Atractylodes macrocephala* | Active ingredient | 0.004% | Alcohol and water |
| *Bletilla striata* | Active ingredient | 0.006% | Alcohol and water |
| *Wolfiporia extensa* | Active ingredient | 0.05% | Alcohol and water |
| *Aconitum carmichaelii* | Active ingredient | 0.0002% | Alcohol and water |
| *Lithospermum erythrorhizon* | Active ingredient | 0.01% | Alcohol and water |
| Alkyl amido betaine | Surfactant | 5.00% | — |
| Sodium lauroyl sarcosinate | Surfactant | 5.00% | — |
| Sodium lauroyl methyl isethionate | Surfactant | 5.00% | — |
| Potassium cocoyl glycinate | Surfactant | 5.00% | — |
| PEG-7 glyceryl cocoate | Thickening agent | 1.00% | — |
| PEG-200 hydrogenated glyceryl palmate | Thickening agent | 1.00% | — |
| Sodium chloride | Viscosity modifier | 1.00% | — |
| Pure water | Carrier, thinner | q.s. | — |

This comparative embodiment provides a mild cleansing composition with active ingredients at concentrations below saturation. The test and comparison results of the comparative embodiment are presented below.

[Experiments with Regard to Near-Saturation, Saturation, and Supersaturation]

Microscopic observation was carried out as follows. The composition in comparative embodiment 13 was thoroughly mixed with water in a weight ratio of 1:1 and then observed under a microscope at a 10-minute and 60-minute time point change after being washed repeatedly with the composition in comparative embodiment 13 within a short time. More specifically, the evaluation results of the degree of radiance (1.4 GU before cleaning, and 1.4 GU after cleaning) indicate that the degree of radiance of the skin did not change significantly, and the microscopic observation also showed no significant cytomorphological change after cleaning. However, it was still able to be seen under the microscope that the degree of radiance was reduced after cleaning.

The experimental results of the saturated embodiment 10 and the unsaturated comparative embodiment 13 with regard to the prevention of excessive cleaning and to protection show that the saturated embodiment 10 not only prevented excessive cleaning of the skin and provided protection for the skin, but also increased the smoothness of the skin, whereas the unsaturated comparative embodiment 13 was not significantly effective in preventing excessive cleaning of the skin or in protecting the skin. The experiments show that the mild cleansing composition nearly saturated, saturated, or supersaturated with an active ingredient according to the present invention is novel and involves an inventive step.

While the present invention has been disclosed above through a number of embodiments, those embodiments are not intended to be restrictive of the scope of the invention. A person of ordinary skill in the art will be able to change or modify the embodiments slightly without departing from the spirit or scope of the invention. The scope of the patent protection sought by the applicant is defined by the appended claims.

What is claimed is:

1. A mild cleansing composition, characterized by comprising:
   at least one surfactant, wherein the at least one surfactant makes up 5 wt % to 70 wt % of the mild cleansing composition, and includes:
   potassium cocoyl glycinate; and
   at least one selected from the group consisting of a long-chain betaine, sodium lauroyl sarcosinate, and sodium lauroyl methyl isethionate; and
   at least one active ingredient present at a concentration near saturation, of saturation, or of supersaturation and capable of improving skin texture, wherein the active ingredient is fat-soluble and physiologically active, making up 0.1 wt % to 10 wt %, and wherein the at least one active ingredient includes:
   at least four extracts selected from the group consisting of 0.10 wt % to 1.80 wt % *Angelica dahurica* extract, 0.10 wt % to 1.80 wt % *Ampelopsis japonica* extract, 0.10 wt % to 1.80 wt % *Atractylodes macrocephala* extract, 0.05 wt % to 0.80 wt % *Bletilla striata* extract and 0.05 wt % to 0.80 wt % *Wolfiporia extensa* extract; and
   at least one selected from 0.05 wt % to 0.80 wt % *Aconitum carmichaelii* extract, and 0.05 wt % to 0.20 wt % *Lithospermum erythrorhizon* extract.

2. The mild cleansing composition of claim 1, wherein the surfactant makes up 10 wt % to 65 wt % of the mild cleansing composition.

3. The mild cleansing composition of claim 1, wherein the active ingredient makes up 0.2 wt % to 6 wt % of the mild cleansing composition.

4. The mild cleansing composition of claim 1, further comprising water.

5. The mild cleansing composition of claim 4, wherein the water makes up 20 wt % to 80 wt % of the mild cleansing composition.

6. The mild cleansing composition of claim 1, further comprising a cosmetic excipient.

7. The mild cleansing composition of claim 6, wherein the cosmetic excipient makes up 0.50 wt % to 10.00 wt % of the mild cleansing composition.

8. The mild cleansing composition of claim 1, wherein an extract of the active ingredient is prepared by a common high-temperature aqueous-solution-based extraction method, an organic-solvent-based extraction method, an ultrasonic extraction method, or a supercritical-fluid-based extraction method.

9. A mild cleansing composition, characterized by comprising:
   at least one surfactant making up 5 wt % to 70 wt % of the mild cleansing composition, and including:
   potassium cocoyl glycinate; and
   at least one selected from the group consisting of a long-chain betaine, sodium lauroyl sarcosinate, and sodium lauroyl methyl isethionate; and
   at least one active ingredient present at a concentration near saturation, of saturation, or of supersaturation and capable of improving skin texture, making up 0.1 wt % to 10 wt %, and wherein the at least one active ingredient includes:
   a combination of 0.10 wt % to 1.80 wt % *Angelica dahurica* extract, 0.10 wt % to 1.80 wt % *Ampelopsis japonica* extract, 0.10 wt % to 1.80 wt % *Atractylodes macrocephala* extract, 0.05 wt % to 0.80 wt % *Bletilla striata* extract and 0.05 wt % to 0.80 wt % *Wolfiporia extensa* extract; and
   at least one selected from 0.05 wt % to 0.80 wt % *Aconitum carmichaelii* extract, and 0.05 wt % to 0.20 wt % *Lithospermum erythrorhizon* extract.

10. The mild cleansing composition of claim 9, wherein the surfactants make up 10 wt % to 65 wt % of the mild cleansing composition.

11. The mild cleansing composition of claim 9, wherein the active ingredients make up 0.2 wt % to 6 wt % of the mild cleansing composition.

12. The mild cleansing composition of claim 9, further comprising water.

13. The mild cleansing composition of claim 12, wherein the water makes up 20 wt % to 80 wt % of the mild cleansing composition.

14. The mild cleansing composition of claim 9, further comprising a cosmetic excipient.

15. The mild cleansing composition of claim 14, wherein the cosmetic excipient makes up 0.50 wt % to 10.00 wt % of the mild cleansing composition.

16. The mild cleansing composition of claim 9, wherein the extract of the active ingredient is prepared by a common high-temperature aqueous-solution-based extraction method, an organic-solvent-based extraction method, an ultrasonic extraction method, or a supercritical-fluid-based extraction method.

* * * * *